(12) United States Patent
Belson et al.

(10) Patent No.: US 8,323,313 B1
(45) Date of Patent: Dec. 4, 2012

(54) SURGICAL INCISION AND CLOSURE APPARATUS WITH INTEGRATED FORCE DISTRIBUTION

(75) Inventors: Amir Belson, Los Altos, CA (US); Eric Storne, Menlo Park, CA (US); Eric T. Johnson, Temecula, CA (US); Robert R. Ragland, Temecula, CA (US); Phillip C. Burke, Pala, CA (US)

(73) Assignee: ZipLine Medical, Inc., Los Altos, CA (US)

( * ) Notice: Subject to any disclaimer, the term of this patent is extended or adjusted under 35 U.S.C. 154(b) by 0 days.

(21) Appl. No.: 13/286,757

(22) Filed: Nov. 1, 2011

(51) Int. Cl.
*A61B 17/08* (2006.01)
*A61D 1/00* (2006.01)

(52) U.S. Cl. ........................................................ 606/216

(58) Field of Classification Search .................... 606/216
See application file for complete search history.

(56) References Cited

U.S. PATENT DOCUMENTS

| | | | |
|---|---|---|---|
| 2,012,755 A | 8/1935 | Muth | |
| 2,747,248 A | 5/1956 | Mercer | |
| 3,487,836 A | 1/1970 | Niebel et al. | |
| 3,516,409 A | 6/1970 | Howell | |
| 3,863,640 A | 2/1975 | Haverstock | |
| 3,926,193 A * | 12/1975 | Hasson | 606/218 |
| 3,933,158 A | 1/1976 | Haverstock | |
| 3,971,384 A | 7/1976 | Hasson | |
| 4,038,989 A | 8/1977 | Romero-Sierra et al. | |
| 4,114,624 A | 9/1978 | Haverstock | |
| 4,526,173 A | 7/1985 | Sheehan | |
| 4,535,772 A | 8/1985 | Sheehan | |
| 4,605,005 A | 8/1986 | Sheehan | |
| 4,676,245 A | 6/1987 | Fukuda | |
| 4,881,546 A | 11/1989 | Kaessmann | |
| 4,905,694 A | 3/1990 | Will | |
| 4,976,726 A | 12/1990 | Haverstock | |
| 5,377,695 A | 1/1995 | An Haack | |
| 5,514,155 A | 5/1996 | Daneshvar | |
| 5,665,108 A | 9/1997 | Galindo | |
| 6,126,615 A | 10/2000 | Allen et al. | |
| 6,176,868 B1 | 1/2001 | Detour | |
| 7,455,681 B2 * | 11/2008 | Wilke et al. | 606/216 |
| 7,645,285 B2 | 1/2010 | Cosgrove et al. | |

(Continued)

FOREIGN PATENT DOCUMENTS

WO  WO 2011/043786 A1  4/2011

OTHER PUBLICATIONS

U.S. Appl. No. 13/414,176, filed Mar. 7, 2012, Belson et al.

(Continued)

*Primary Examiner* — Melanie Tyson
(74) *Attorney, Agent, or Firm* — Wilson, Sonsini, Goodrich & Rosati (57) ABSTRACT

Apparatus for closing a surgical incision include a base having left and right panels, a force distribution structure coupled to each panel, and a closure component which releasably attaches to the force distribution structure to draw the inner edges of the panels together in order to close adhered tissue edges. The force distribution structures allow the inner edges of the panels to expand while restraining expansion of the outer edges of the panels and limiting elongation of the lateral dimension of the panels. The incision closure apparatus may be placed on skin or other tissue prior to forming the incision to be available to close said incision at the end of the surgical procedure.

15 Claims, 5 Drawing Sheets

U.S. PATENT DOCUMENTS

| | | | |
|---|---|---|---|
| 2005/0020956 A1* | 1/2005 | Lebner | 602/42 |
| 2005/0234485 A1 | 10/2005 | Seegert et al. | |
| 2006/0200198 A1 | 9/2006 | Riskin et al. | |
| 2007/0026078 A1 | 2/2007 | Almarsson et al. | |
| 2007/0088339 A1 | 4/2007 | Luchetti | |
| 2007/0141130 A1 | 6/2007 | Villanueva et al. | |
| 2007/0260278 A1 | 11/2007 | Wheeler et al. | |
| 2008/0033334 A1 | 2/2008 | Gurtner et al. | |
| 2008/0081951 A1 | 4/2008 | Frasier et al. | |
| 2008/0114396 A1* | 5/2008 | Cory et al. | 606/216 |
| 2008/0287864 A1 | 11/2008 | Rosenberg | |
| 2009/0036922 A1 | 2/2009 | Riskin et al. | |
| 2009/0099496 A1 | 4/2009 | Heegard et al. | |
| 2009/0299255 A1 | 12/2009 | Kazala et al. | |
| 2009/0299257 A1 | 12/2009 | Long et al. | |
| 2009/0299303 A1 | 12/2009 | Seegert | |
| 2010/0121286 A1 | 5/2010 | Locke et al. | |
| 2012/0016410 A1 | 1/2012 | Belson et al. | |
| 2012/0046691 A1 | 2/2012 | Belson et al. | |

OTHER PUBLICATIONS

International search report and written opinion dated Jul. 29, 2011 for PCT/US2011/034649.

International search report and written opinion dated Oct. 21, 2011 for PCT Application No. US2011/40213.

International search report dated Jul. 30, 2010 for PCT/US2010/000430.

* cited by examiner

SURGICAL INCISION AND CLOSURE APPARATUS WITH INTEGRATED FORCE DISTRIBUTION

BACKGROUND OF THE INVENTION

1. Field of the Invention

The present invention relates generally to medical apparatus and methods. More particularly, present invention relates to apparatus and methods for forming and closing surgical incisions.

Surgical closure devices including an adhesive based patch with right and left panels are known. Of particular interest of the present invention, such devices are described in co-pending, commonly owned PCT application US 2010/000430, full disclosure which is incorporated herein by reference. As described in the PCT application, an adhesive patch is placed over a patient's skin at a site where it is desired to form a surgical incision. After the patch is placed, an incision is formed along an axial line extending through the middle of the patch. After it is formed, the incision can be opened to perform a desired procedure, and after the procedure is completed the incision may be closed by drawing the inner edges of the panels together with a clip, zipper, or other closure member.

The principal objective of such surgical closure devices is to improved healing and reduce scaring from the incision. This objective, however, has been inhibited by certain characteristics of the presently available devices. For example, the tissue edges are not always brought together along an even line, which can increase the eventual scaring. Many such closure devices do not have the ability to adjust the closure force or distance on the tissue edges, limiting the ability to slightly "pucker" tissue which has been found to reduce scaring. Other shortcomings of the available incision and wound closure devices include difficulty of use and inability to conform to tissue manipulation during subsequent surgical protocols, i.e. those devices which are sufficiently rigid to securely close the tissue are often unable to conform to the tissue movement during the surgical procedure.

For these reasons, it would be desirable to provide improved surgical incision closure devices and methods for their use. It would be particularly desirable to provide incision closure devices which are able to adhere to the tissue, allow formation of the incision, conform to the deformation of the tissue during a subsequent surgical procedure, and provide controlled closure of the adjacent tissue edges subsequent to the procedure. In particular, it would be desirable if the incision closure devices were able to provide for the control and the uniform distribution of closure forces on the tissue edges while causing minimum restraint or stretching of the tissue during the surgical procedure. At least some of these objectives will be met by the inventions described below.

2. Description of the Background Art

Co-pending, commonly owned PCT application US 2010/000430 as been described above. Other surgical closure devices are described in the following U.S. Pat. Nos. 2,012,755; 3,516,409; 3,863,640; 3,933,158; 4,114,624; 4,535,772; 4,676,245; 4,881,546; 4,905,694; and 5,377,695. Commercial incision closure devices available from Ethicon, a division of Johnson & Johnson, under the trade name Ethizip™ temporary abdominal wound closure device.

SUMMARY OF THE INVENTION

The present invention provides improved apparatus and methods for closing wounds, particularly wounds resulting from incisions performed during surgical procedures. The incisions would usually be formed in a patient's skin, such as through the abdomen, but in some cases could also be on internal organs, within the oral cavity, within body cavities, or alike.

The devices and methods of the present invention will present minimum disruption of or interference with the surgical procedure which is performed after the incision is made. In particular, the devices and methods will permit the opposed edges of the incised tissue to be opened, stretched, and freely deformed with minimal restraint resulting from the presence of the closure device. Once the procedure has been completed, however, the devices and methods of the present invention will provide for a uniform distribution of closure forces to draw the tissue edges together in a manner which and minimize scaring. In particular, the closure devices can draw the tissue edges together at a slightly closer spacing than initially present at the forming of the incision in order to upwardly evert the tissue edges cause a "pucker" which can reduce scaring.

In a first aspect of the present invention, an incision closure appliance comprises a base including a left panel and a right panel. Each panel has a tissue adherent lower surface, an upper surface, an inner edge, and an outer edge. The lower tissue adherent surface will typically be coated at least partially with a common tissue-adherent adhesive such as those used in surgical bandages and patches.

The incision closure appliance further includes a force distribution structure coupled to each panel (i.e. each panel will have at least one force distribution structure coupled thereto), where each force distribution structure is adapted to allow axial expansion of the panel along the inner edge while limiting lateral expansion over the entire length and axial expansion along the outer edge. By permitting axial expansion of the panel along the inner edge, the tissue edges are minimally constrained to allow the tissue to deform when stretched during the surgical procedure. Conversely, by limiting both lateral expansion and axial expansion along the outer edge, the panel will be able to apply a controlled and distributed closure force when the panels are drawn together after the surgical procedure is complete, as described in more detail below.

The incision closure appliance still further includes a closure component which releasably attaches to the force distribution structure to draw the inner edges of the panels together after they had been adhered to the tissue on opposite sides of an incision and the surgical procedure completed. Each panel of the base will typically comprise an at least partially elastic matrix, typically having an isotropic elasticity (i.e. the panel stretches evenly in all directions) but optionally having an anisotropic elasticity (where the matrix stretches preferentially in one direction or over a portion thereof). The elastic matrix may comprise an elastomeric membrane or sheet (for example Polyurethane sheet or Thermo Plastic Elastomers (TPE)), a woven fabric (typically woven at least partially from elastomeric filaments, threads, or fibers), a spun fabric, or the like. In certain embodiments, the elastomeric matrix may comprise a fabric woven from both elastic elements (typically threads, filaments, fibers, or the like) and having inelastic elements disposed along the outer edge and extending laterally there across in order to provide the expansion characteristics described above with respect to the force distribution structure. That is, in some cases, the force distribution structure may include or consist of inelastic elements woven or otherwise incorporated within a fabric membrane.

Typically, the force distribution structure will comprise a separate component of the incision closure appliance, for example including a spine disposed axially adjacent to the outer edge of the panel and a plurality of axially spaced-apart supports disposed laterally and extending from the spine toward the inner edge of the panel. Such a "comb-like" structure will typically be formed from flexible but non-distensible materials so that the elements can flex together with the tissue deformation but will not stretch along their lengths so that they may provide dimensional stability in the lateral direction as well as along the outer edge of the panel. Examples of such materials include Nylon, Polypropylene, Polyethylene and Polycarbonate or other thermo polymers. Notably, the force distribution structure will not limit the axial stretching of the inner edge of the panel in order to provide the desired expansibility and conforms to the tissue during the surgical procedure. Such separate force distribution structures may be attached to the upper surface of the panel, or alternatively may be embedded in or laminated within the panel. Typically, the force distribution structure will not extend into or past the lower surface of the panel so that it will not interfere with adherence of the panel to the skin or other tissue.

The assembly of the base panels and the force distribution structures will typically be carried on a removable backing which covers and protects the adherent surface of the panels prior to use. The adherent backing may be removed in order to apply the base to the skin or other tissue at the site of the surgical intervention. Additionally, the right and left panels will typically be held together by removable tabs or other removable covers or structures in order to hold the inner edges of the panel at a pre-determined distance or spacing as they are being adhered to the tissue. The cover or tabs may then be removed to leave the panels in place but unconnected prior to forming the surgical incision therebetween.

A preferred construction of the closure component comprises a right engagement member, a left engagement member, and a plurality of lateral struts holding the engagement members laterally apart by a pre-determined distance. The right engagement member is adapted to releasably engage the supports of the right panel along an inner edge thereof, and the left engagement member is adapted to releasably engage the supports of the left panel along an inner edge thereof. In the specific embodiments, at least some of the supports of the force distribution component will have cleats near their inner edges, and the engagement members will have slots which receive the cleats. After the surgical intervention is complete, the closure component may then be placed over the force distribution structure with the cleats on one side first being engaged by an engagement member and then the opposite engagement member being pulled over the cleats on the opposite side. Optionally, the lateral struts of the closure component may be adjustably connected to at least one of the engagement members to permit adjustment of the spacing between said panels.

Optionally, the closure appliance of the present invention may further comprise a securing layer which is adapted to be placed over the assembly of the base and the closure component after the assembly has been secured over an incision on a patient's skin and the surgical procedure has been completed. A securing layer will typically have a self-adhesive lower surface which can be placed over the assembly of the base and closure component to help secure it in place and to maintain cleanliness. The securing layer may optionally have openings to permit access to the wound for observation, delivery of antiseptics, and the like.

In a further aspect of the present invention, methods for forming an incision in tissue comprise providing an incision closure appliance as described above. The right and left panels of the appliance are adhered to the patient's skin, where the inner edges of the panels are spaced-apart by a pre-selected distance typically from 0.5 mm to 15 mm. An incision (typically linear) is formed in the tissue or skin surface between the inner edges of the panels, and the edges of the incised tissue are then separated to perform a desired surgical procedure. The inner edges of the panels can stretch and conform along with movement and deformation of the tissue edges while the outer edge and lateral extent of each panel remain dimensionally stable. After the procedure is complete, the closure component is secured to the force distribution structure to draw the inner edges of the panels back together. Optionally, the closure component has dimensions (or an adjustable inter-panel spacing) which draw the tissue edges closer together than they were immediately after the incision was formed. Such drawing together of the tissue causes the edges to evert and the tissue to "pucker" which can reduce scarring.

DETAILED DESCRIPTION OF THE INVENTION

The apparatus and methods of the present invention will be used during both the formation and the closure of surgical incisions made to a patient's skin or other tissue during surgical procedures. As described hereinafter, the direction of the incision will define both "axial" and "lateral" directions as those terms are used herein. Most incisions will be made along a generally straight line which will define the axial direction. The lateral direction will generally be across the axial direction, typically but not necessarily being perpendicular or normal to the axial direction. Most incisions will be generally linear but in some cases the incisions could be curved or have other geometries. The term "axial" will then apply to the direction of the incision at any particular location, resulting in lateral directions which could also vary.

Figure 1:
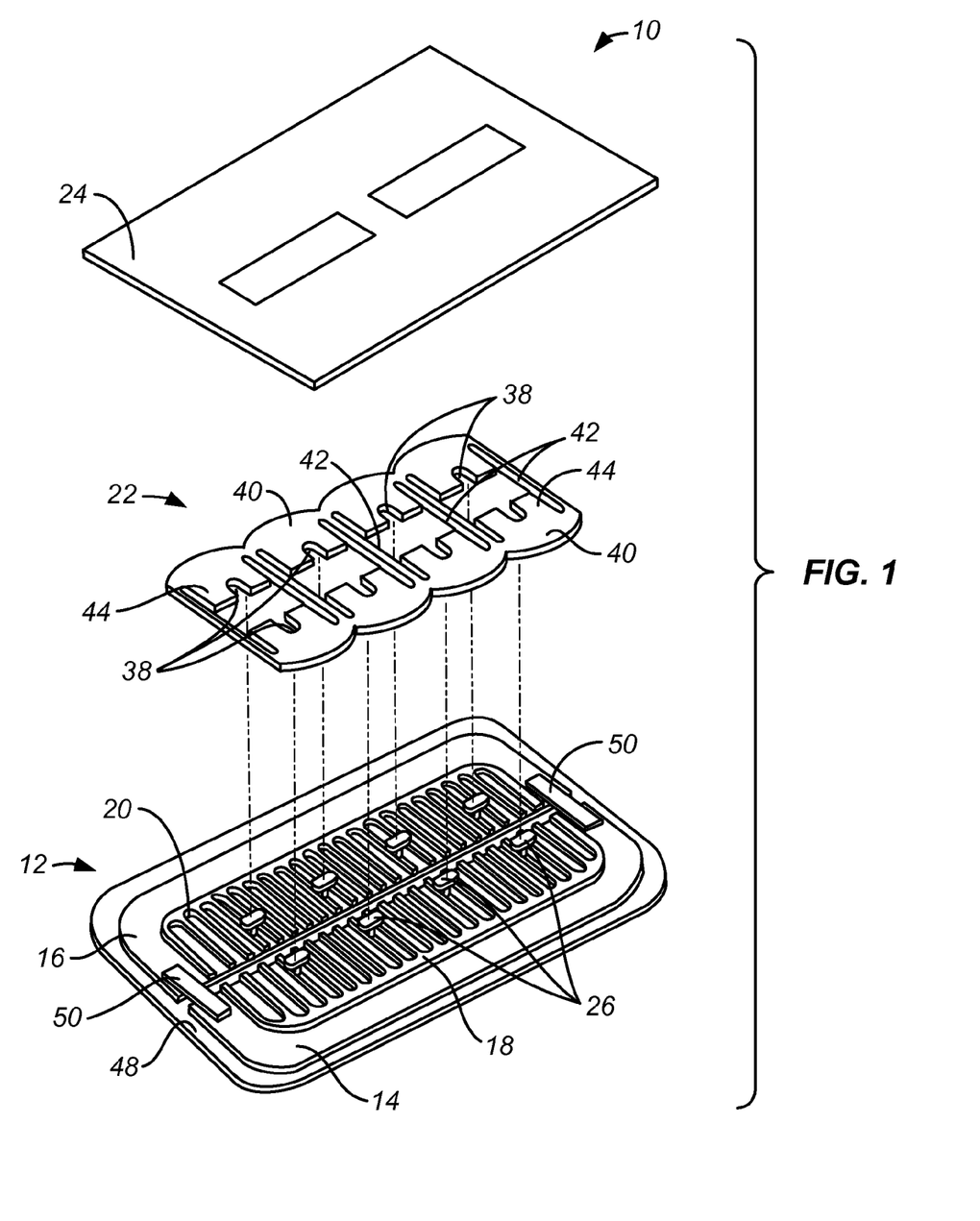
FIG. 1 is an exploded view of an incision closure appliance constructed in accordance with the principles of the present invention.
Figure 2:
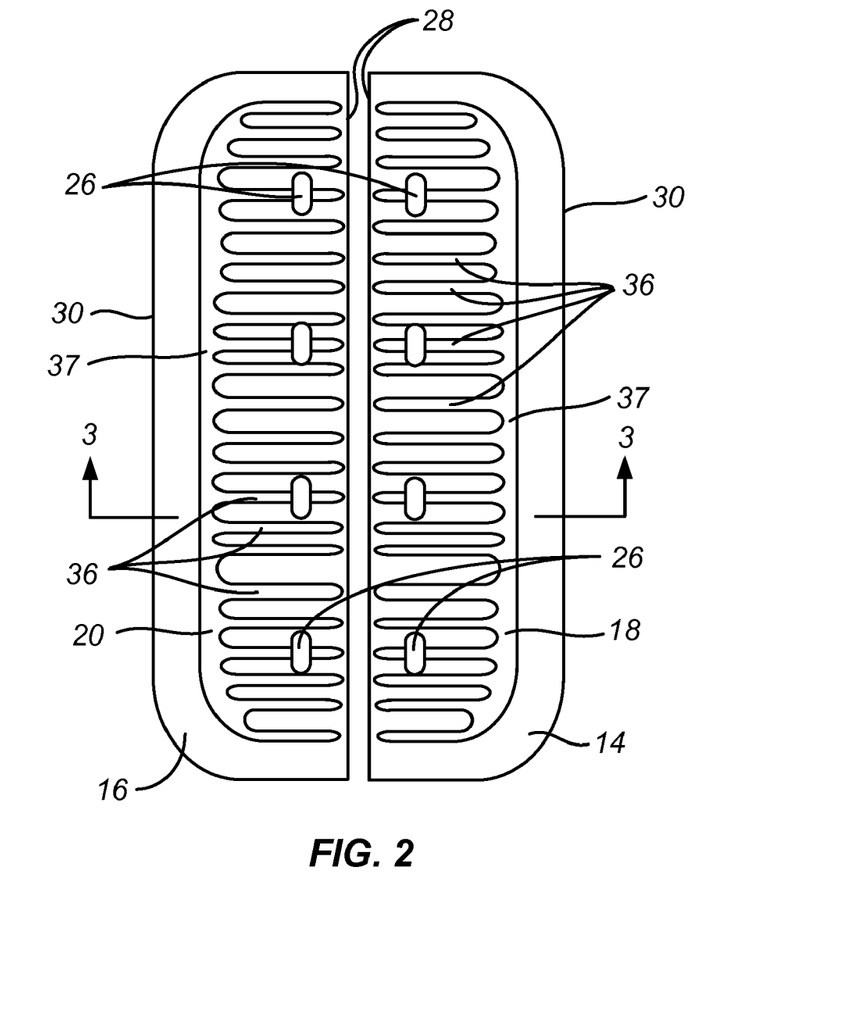
FIG. 2 is a top view of the assembly of a base and a force distribution structure which is part of the incision closure appliance.
Figure 3:
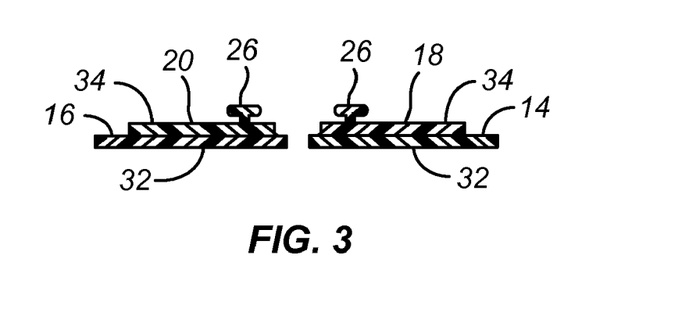
FIG. 3 is a cross-sectional view taken along line 3-3 of FIG. 2.

Referring now to FIGS. 1-3, an incision closure appliance 10 comprises a base assembly 12 including a right panel 14 and a left panel 16. A right force distribution structure 18 is secured to the right panel 14, typically by laminating the force distribution structure to an upper surface of the panel, and a left force distribution structure 20 is similarly attached to an upper surface of the left panel 16. The incision closure appliance further comprises a closure component 22 which is removably attachable to the right and left forced distribution structures 18 and 20 in order to close an incision, as described in more detail below, and the appliance is completed with an optional securing layer 24 which may be placed over the combined base assembly 12 and closure component 22 after they have been secured to the patient and the incision has been closed by drawing the panels together using the closure component.

The closure component 22 is intended and adapted to draw the inner portions of the force distribution structures 18 and 20 inwardly toward each other to close a surgical incision which has been formed therebetween. In the illustrated embodiment, a plurality of cleats 26 are formed on lateral supports 36 which are held axially by spine 37 of the force distribution structures 18 and 20. The cleats 26 are received in slots 38 formed along inner edges of opposed engagement members 40 of the closure component 22. The opposed engagement members 40 are held together by lateral struts 42 so that the engagement members are held at a fixed, laterally spaced-apart distance (in other embodiments the spaced-apart distance may be adjustable). The slots 38 are preferably formed on flexible tab-like structures 44 which allow the slots to be pulled upwardly over the corresponding cleats in order to secure the closure component 22 over the force distribution structures 18 and 20.

The lower surfaces 32 of each panel 18 and 20 will typically be covered with a pressure-responsive adhesive, where the adhesive is initially covered with a protective layer 48 which may be peeled away immediately prior to use. Additionally, pull-away tabs 50 or other similar structures may be provided in order to hold the right and left panels 14 and 16 together at a pre-determined spaced-apart distance after the layer 48 has been removed but prior to adhering the panels to a patient's skin or other tissue surface. It is important that the distance between the inner edges 28 of each panel 14 and 16 be maintained as close as possible to the original target spacing so that the tissue edges, when closed by the closure component 22, will be precisely brought together, typically with a slight eversion.

Figure 4:
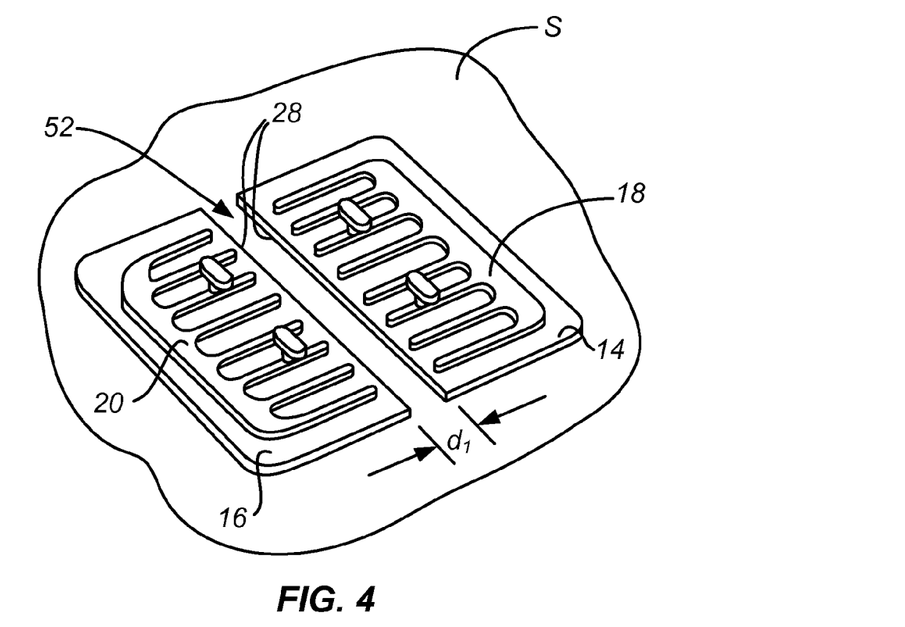
FIGS. 4-7 illustrate use of the incision closure appliance of the present invention for forming and closing an incision in a patient's skin.

Referring now to FIGS. 4 through 7, a protocol for both forming an incision and subsequently closing the incision in accordance with the principles of the present invention will be described. Initially, the right and left panels 14 and 16 are placed on the patient's skin followed by reference letter S, as shown in FIG. 4. The panels 14 and 16 are applied by first pulling away the protective layer 18 and placing the panels onto the tissue, after which time the tabs 50 may be removed, leaving an incision path 52 defined between the inner edges 28. The spacing of the inner edges 28 will be selected to provide a fixed, pre-determined distance $d_1$.

Figure 5:
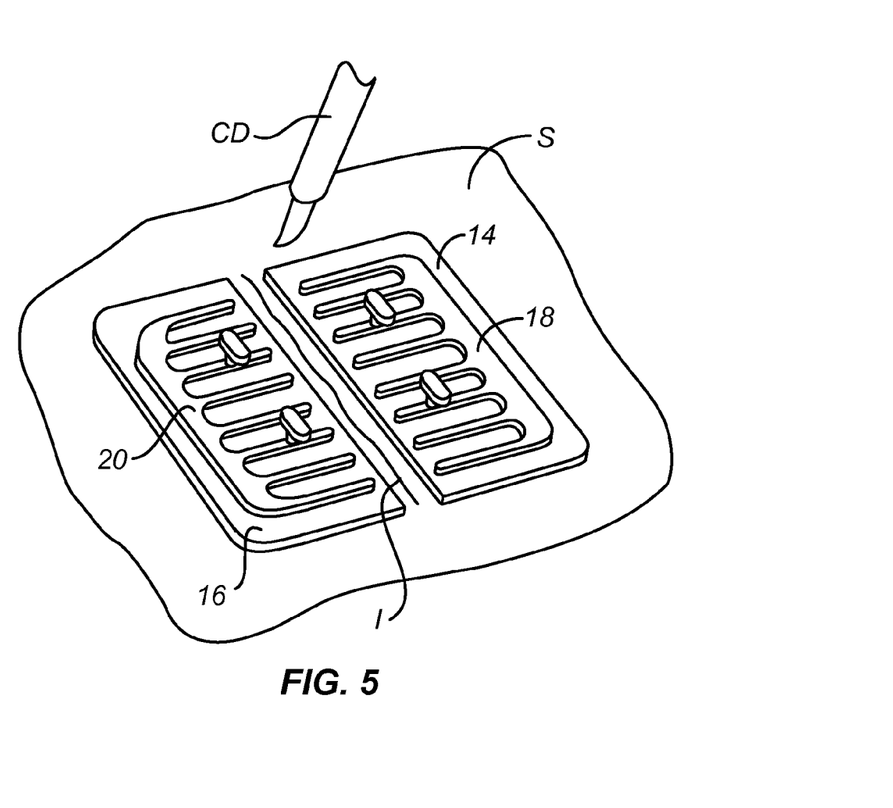

After the right and left panels 14 and 16 are in place, an incision I can be formed in the space between the panels using a scalpel or other surgical cutting device CD, as shown in FIG. 5.

Figure 6:
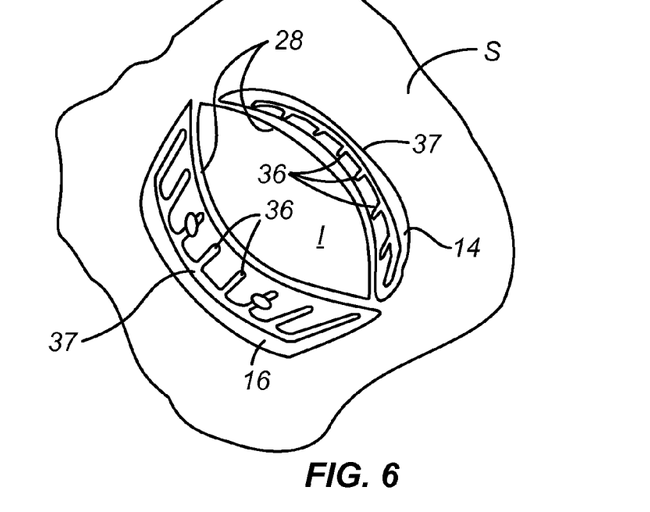

After the incision I is made, a surgical procedure may be performed by opening the inner edges of the incision which in turn deforms the inner edges 28 of the right and left panels 14 and 16, as shown in FIG. 6. As the inner most ends of the supports 36 are not connected, they are free to separate and allow the elastic matrix of the right and left panels 14 and 16 to expand, as clearly in FIG. 6. The dimensional stability of the remainder of the panels, however, will be preserved by the lateral supports 36 as well as the axial spines 37 which do not elongate under the influence of the force applied by stretching opening the incision.

Figure 7:
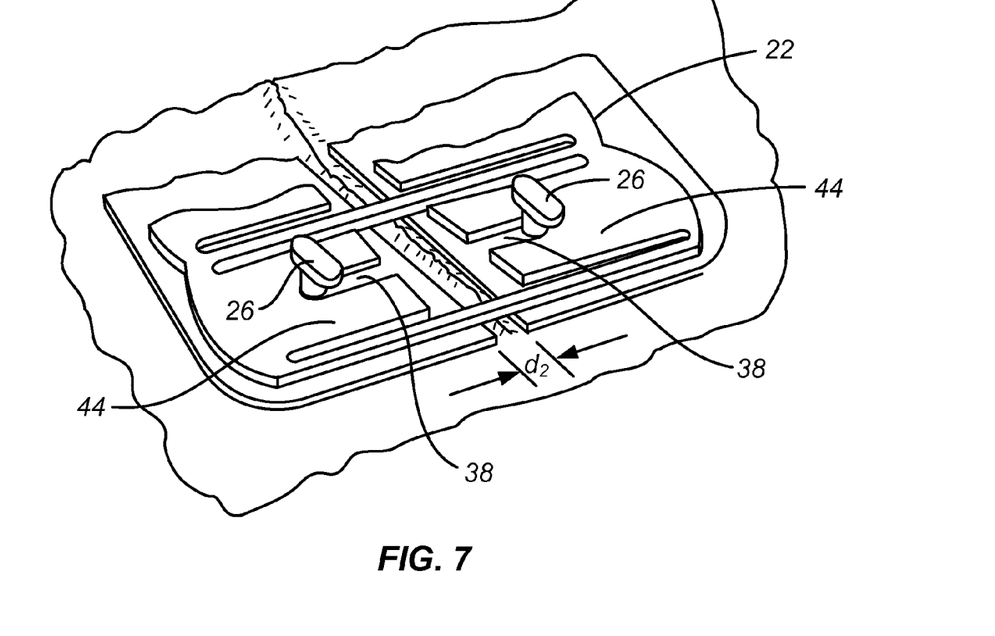

After the surgical procedure is complete, the closure component 22 will be secured over the force distribution structures 18 and 20, as illustrated in FIG. 7. In particular, the slots 38 in the tab-like structures 44 are engaged over opposed cleats 26 in order to draw opposed edges of the panels as well as of the tissue incision together. By properly spacing the depth of the slots 38, the closure component 22 can be tailored so that the panels 14 and 16 are brought together by a pre-selected distance $d_2$. Typically, the distance $d_2$ will be less than the initial separation $d_1$ so that the inner edges of the tissue are brought together to cause the tissue edges along the incision to slightly evert (pucker upwardly) which can improve healing and reduce scarring.

Figure 8:
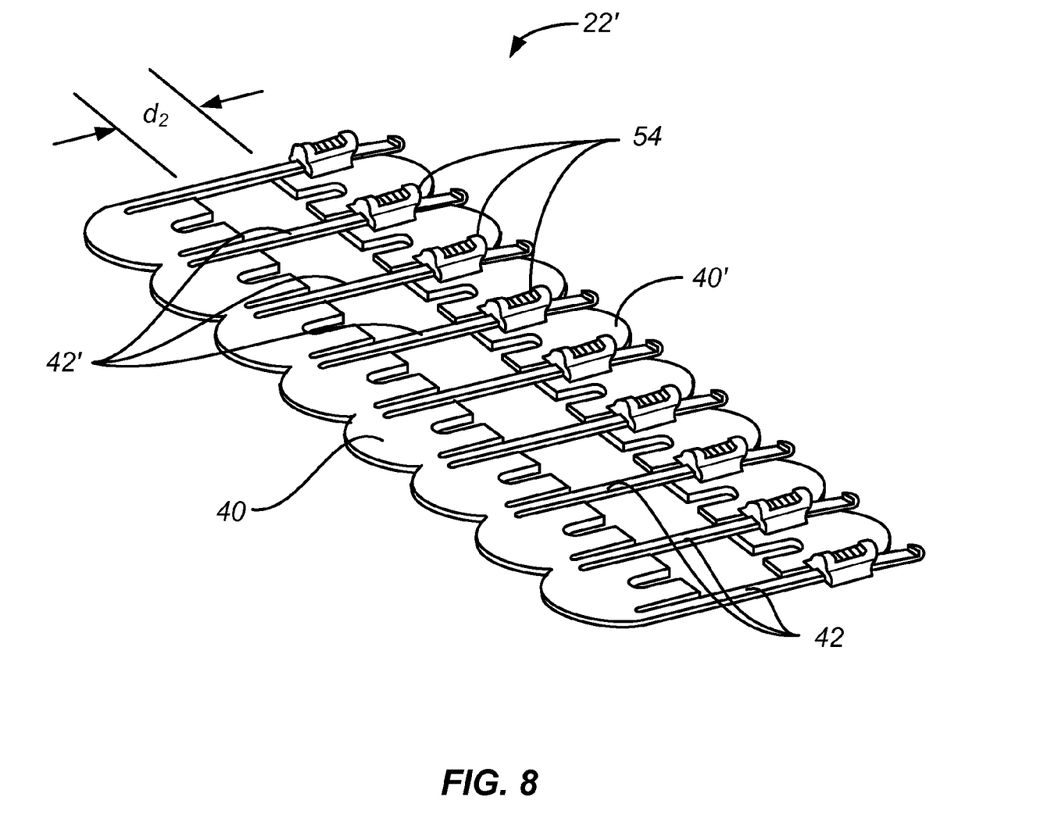
FIG. 8 illustrates an alternative construction of a closure component for the closure appliance of the present invention.

Optionally, as shown in FIG. 8, a closure component 22' may include engagement members 40', where one end of each lateral strut 42' is joined by an adjustable clasp or other mechanism 54 so that the distance between the inner edges of the opposed engagement members 40' can be adjusted in order to increase or lessen the distance $d_2$ therebetween.

What is claimed is:

1. An incision closure appliance comprising:
   a base including a left panel and a right panel, each panel having a tissue adherent lower surface, an upper surface, an inner edge, and an outer edge;
   a force distribution structure coupled to each panel, wherein each force distribution structure includes a spine disposed axially adjacent the outer edge to limit axial expansion along the outer edge and a plurality of axially spaced-apart supports extending laterally from the spine toward the inner edge to limit lateral expansion while allowing axial expansion along the inner edge; and
   a closure component which releasably attaches to the force distribution structure to draw the inner edges of the panels together after they are adhered to tissue on opposite sides of an incision.

2. An incision closure appliance as in claim 1, wherein each panel of the base comprises an elastic matrix.

3. An incision closure appliance as in claim 2, wherein the elastic matrix comprises an elastomeric membrane, a woven fabric, or a spun fabric.

4. An incision closure appliance as in claim 2, wherein the elastic matrix comprises a fabric woven from elastic elements and having inelastic elements along the outer edge and extending laterally thereacross.

5. An incision closure appliance as in claim 1, wherein the spine and supports are formed from flexible, non-distensible materials.

6. An incision closure appliance as in claim 1, wherein the spine and supports are formed integrally as a comb-like structure.

7. An incision closure appliance as in claim 1, wherein the force distribution structures are embedded in or laminated to the upper surface of each panel.

8. An incision closure appliance as in claim 1, further comprising a removable space-maintainer which holds the right and left panels at a fixed distance while they are being adhered to tissue.

9. An incision closure appliance as in claim 1, wherein the closure component comprises a right engagement member, a left engagement member and a plurality of lateral struts holding the engagement members laterally apart by a predefined distance, wherein the right engagement member is adapted to releasably engage the supports of the right panel along the inner edge and the left engagement member is adapted to releasably engage the supports of the left panel along the inner edge.

10. An incision closure appliance as in claim 9, wherein at least some of the supports have cleats near the inner edge and the engagement members have slots which receive the cleats.

11. An incision closure appliance as in claim 9, wherein the lateral struts are adjustably connected to at least one of the engagement members to permit adjustment of the predefined distance.

12. An incision closure appliance as in claim 1, further comprising a securing layer adapted to be placed over an assembly of the base and the closure component after the assembly has been secured over an incision on a patient's skin.

13. An incision closure appliance as in claim 12, wherein the securing layer has an inner self-adhesive surface.

14. A method for forming an incision in tissue, said method comprising:
    providing an incision closure appliance as in claim 1;
    adhering the right and left panels of the base to a surface of the tissue, wherein the inner edges of the panels are spaced-apart by a preselected distance;
    forming the incision in the tissue surface between the inner edges of the panels;
    separating the incised tissue edges to perform a procedure, wherein the inner edges of the panels can stretch and conform along with the tissue edges while the outer edge and lateral extent of each panel remain dimensionally stable; and
    securing the closure component to the force distribution structure to draw the inner edges of the panels back together.

15. A method as in claim 14, wherein the closure component has dimensions which draw the tissue edges closer together than they were immediately after the incision.

* * * * *